United States Patent [19]
Reif

[11] Patent Number: 5,855,603
[45] Date of Patent: Jan. 5, 1999

[54] SUTURE RING FOR HEART VALVE PROSTHESIS

[75] Inventor: Thomas H. Reif, Vero Beach, Fla.

[73] Assignee: Republic Medical Inc., Vero Beach, Fla.

[21] Appl. No.: 712,672

[22] Filed: Sep. 13, 1996

Related U.S. Application Data

[62] Division of Ser. No. 36,662, Mar. 24, 1995, Pat. No. Des. 376,206, and a division of Ser. No. 53,158, Apr. 15, 1996.

[51] Int. Cl.$^6$ ........................................................ A61F 2/24
[52] U.S. Cl. .............................................. 623/2; 606/153
[58] Field of Search .................................. 623/1, 2, 661, 623/900, 191, 194, 195, 198, 151, 153

[56] References Cited

U.S. PATENT DOCUMENTS

| | | | |
|---|---|---|---|
| 3,938,197 | 2/1976 | Milo | 623/2 |
| 4,114,202 | 9/1978 | Roy et al. | 623/2 |
| 4,489,446 | 12/1984 | Reed | 623/2 |
| 5,178,633 | 1/1993 | Peters | 623/2 |
| 5,397,348 | 3/1995 | Campbell et al. | 623/2 |
| 5,593,435 | 1/1997 | Carpentier et al. | 623/2 |

FOREIGN PATENT DOCUMENTS

| | | | |
|---|---|---|---|
| 996304 | 9/1976 | Canada | 623/2 |

Primary Examiner—Mary Beth Jones
Assistant Examiner—Francis K. Cuddiny
Attorney, Agent, or Firm—Albert H. Reuther

[57] ABSTRACT

A heart valve stiffening ring having a clasp with first and second radial ends interengageable complementary to each other from unlocked position into interlocked position relative to annular members the heart valve and fabric tube respectively cloth wrapped around the suture heart valve stiffening ring as well as a filler ring as an outer annular ring of material are fitted concentrically around the metal stiffening ring per se and collectively are surrounded by the fabric tube of cloth wrapped around the heart valve locking ring and a filler ring surrounding the heart valve radially inwardly thereof. The locking ring serves as a stiffening ring located radially intermediate the filler ring and heart valve locking ring surrounded by the fabric tube respectively cloth wrapped around the assembly of the suture ring collectively therewith. At least two suture lines fix the fabric tube in place. The assembled heart valve prosthesis is rotatable and provides for an orifice ring having a relatively large internal diameter. As a result, fewer and more easily manufactured components are required with more rapid assembly. Also, the suture ring is prevented from being inadvertently separated from the subassembly during implantation.

10 Claims, 2 Drawing Sheets

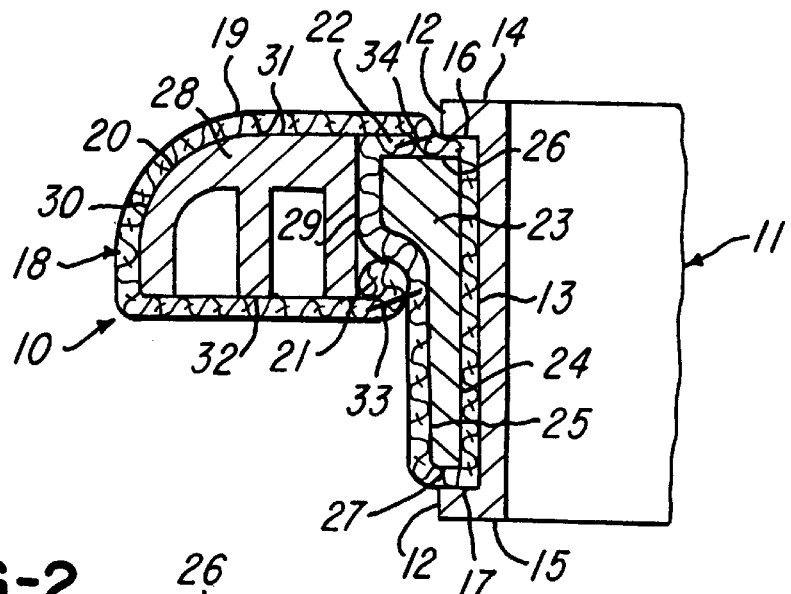
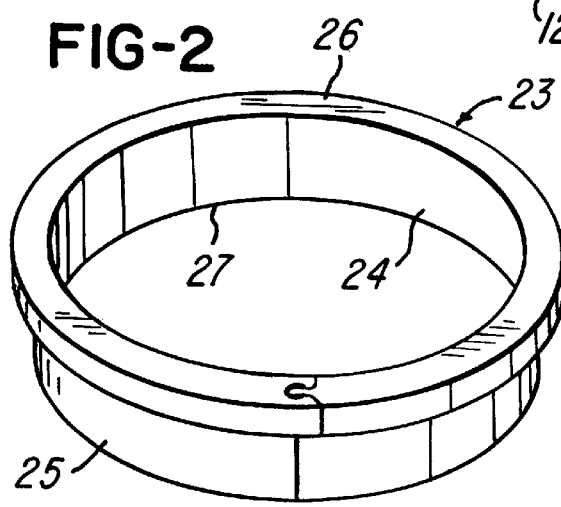
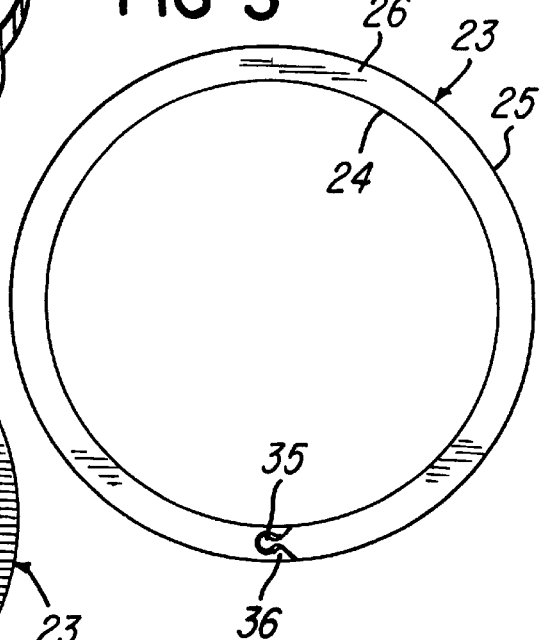
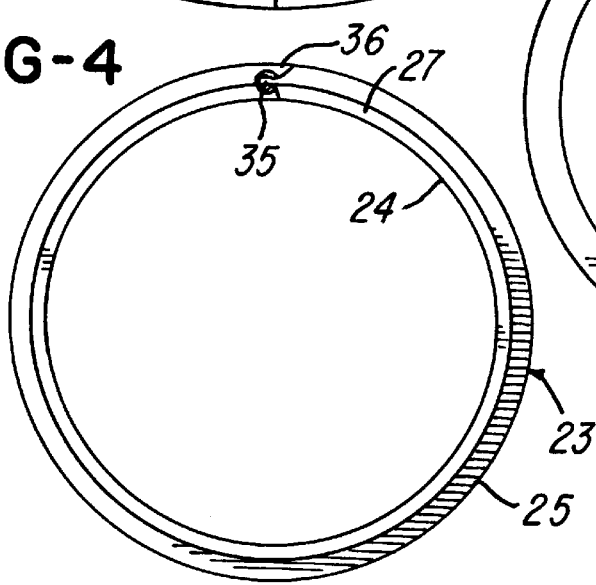

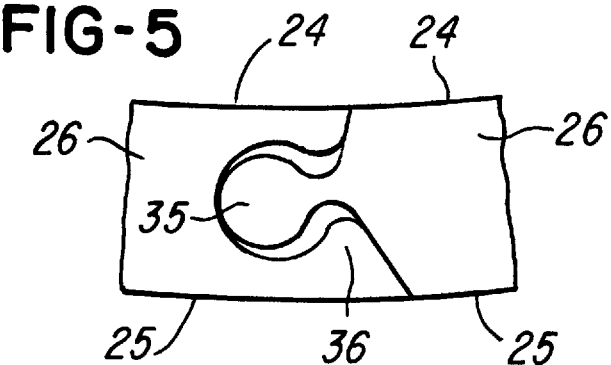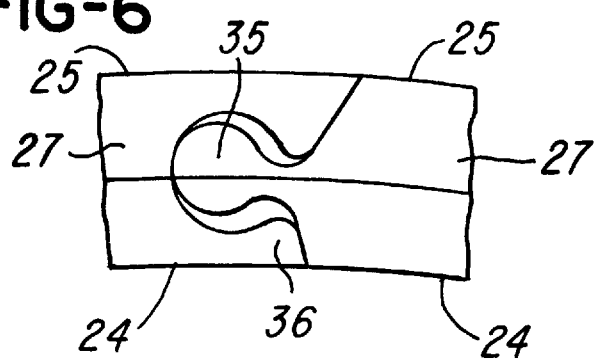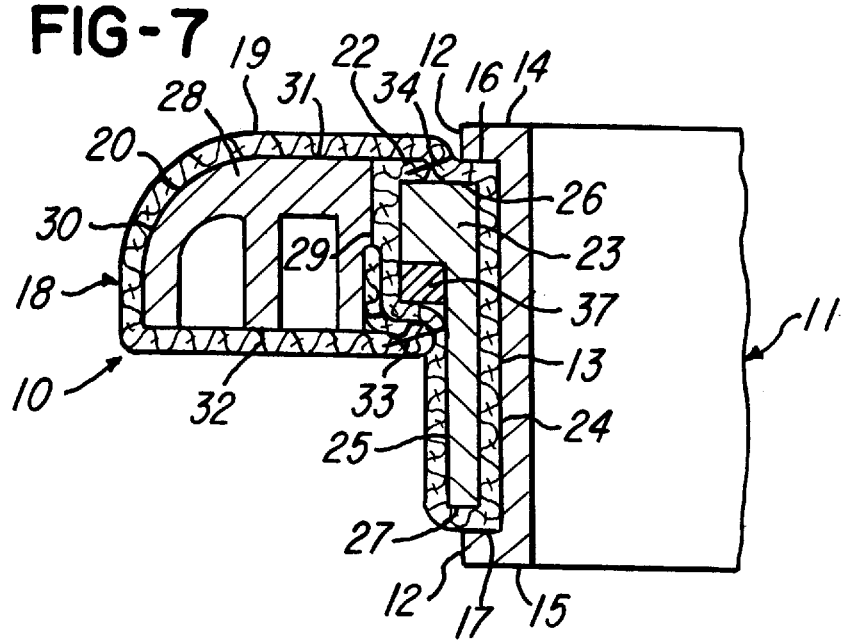

SUTURE RING FOR HEART VALVE PROSTHESIS

This is a divisional application based upon copending Design Application Ser. No. 29/036,662-Reif filed Mar. 24, 1995, now U.S. Design Pat. No. D-376-206-Reif dated Dec. 3, 1996 as well as Divisional Design Ser. No. 29/053,158-Reif filed Apr. 15, 1996 based thereon, and entitled Heart Valve Locking Ring, respectively.

BACKGROUND OF THE INVENTION

1. Field of the Invention

The present invention relates to heart valve protheses, and more particularly, to suture rings for supporting heart valve protheses.

2. Description of the Prior Art

There are two types of heart valve prostheses, biological and mechanical. The medical indications for heart valve replacement are the same for both types. Examples include rheumatic heart disease, congenital anomalies, and myocardial infarction.

Unidirectional flow is the primary function of heart valve prostheses. This is usually accomplished by fashioning rigid or flexible leaflets, free to articulate within certain limitations, within an annular shaped frame, frequently referred to as an orifice ring. The restrained motion of these leaflets causes the flow to be essentially unidirectional, mimicking the natural function of native heart valves.

While the features of the present invention can be used in either biological or mechanical valves, for purposes of facilitating explanation thereof, the present prior art disclosure dissertation will be limited to mechanical valves, such as disclosed in U.S. Pat. Nos. 4,276,658-Hansen dated Jul. 7, 1981, 4,689,046-Bokros dated Aug. 25, 1987 and 4,950, 287-Reif dated Nov. 12, 1991. The leaflets of mechanical valves are usually constructed of pyrolytic carbon or a composite of pyrolytic carbon and a substrate, such as graphite or titanium. The leaflets are typically constrained within an orifice ring also constructed of the same materials. In most cases the orifice ring is deformed in order to insert the leaflets during manufacture. Therefore, it is desirable for the orifice ring to be somewhat compliant. If the orifice ring is too stiff, a significant percentage may be permanently damaged during the insertion process. It is also desirable to maximize the internal diameter of the orifice ring, since this reduces the pressure gradient through the valve, reducing the work that the heart must perform during each stroke.

The orifice ring with the inserted leaflets is often referred to as a subassembly. The subassembly is usually attached to the heart by using a biocompatible fabric material, such as Dacron™. The fabric material is usually purchased or fashioned into a tubular configuration. There are several methods of fixation of the fabric material to the subassembly. One possibility is disclosed in U.S. Pat. No. 3,781,969-Anderson dated Jan. 1, 1974, where the subassembly is placed inside of the fabric tube and a heat shrinkable plastic band is placed around the outside diameter of the fabric tube. The fabric material is then folded into an annular configuration often referred to as the suture ring. Sometimes annular shaped filler rings, often constructed of Teflon™ or Silastic™, are inserted within the folded portion of the fabric tube in order to make the suture ring larger and/or more compliant. It is desirable that a suture ring be rotatable relative to the subassembly, as this feature greatly facilitates implantation into the heart. The use of a heat shrinkable plastic band is one method of achieving rotatability.

Significant forces are applied to the suture ring during both the surgical implantation of the heart valve and during its service life in the body. These forces are transmitted to the leaflets via the orifice ring. It is possible, therefore, to damage the subassembly both during and after implantation. The use of a heat shrinkable plastic band requires that the orifice ring have substantial stiffness. This makes the insertion of the leaflets more difficult and reduces the internal diameter of the orifice ring, both of which are undesirable. Since pyrolitic carbon is a preferred material for the orifice ring, and since it is much more compliant than metal (about 7.5 times more compliant than steel and about 3.8 times more compliant than titanium), it is apparent that both of these problems can be overcome by using a metal stiffening ring around the outside diameter of the subassembly.

U.S. Pat. Nos. 5,071,431-Sauter et al dated Dec. 10, 1991, uses a continuous metal stiffening ring. The inside diameter of the stiffening ring is in direct proximity to the outside diameter of the subassembly, but not in direct contact with it. The inside diameter of the fabric tube is in direct contact with the outside diameter of the stiffening ring and continuous metal fastener bands are used at the proximal and distal ends of the stiffening ring in order to fix the fabric tube to the stiffening ring. This stiffening ring of U.S. Pat. No. 5,071,431 uses a metal split ring as means to prevent the stiffening ring from disengaging from the subassembly and to provide some control over the rotatability of the subassembly within the suture ring. In practice, the assignee of U.S. Pat. No. 5,071,431 with this stiffening ring uses a metal wire for this purpose. The outside diameter of the orifice has a small groove, the inside diameter of the locking ring has a similar small groove, and the metal wire passes within this potential resultant groove space. Therefore, the outside diameter of the orifice ring is constrained by the stiffening ring only over the small contact area from the wire. The disadvantage to this method of constraint is that it requires the orifice ring to be thicker than it would be if the constraint were to be applied over a larger portion of the external diameter of the orifice ring. This is because the leaflets transfer significant loads to the orifice ring, when the leaflets are in the closed position. For the same loading conditions from the leaflets, the larger the area of constraint on the outside diameter of the orifice ring, the lower the stress in the orifice ring. Increasing the thickness of the orifice ring results in a decrease in the inside diameter of the orifice ring, which is an undesirable effect.

Similar arguments can be used to discount the effectiveness of the continuous metal stiffening ring disclosed in U.S. Pat. No. 5,397,348-Campbell et al dated Mar. 14, 1995. In this disclosure, the stiffening ring contacts the subassembly only along the first and second axial ends of the stiffening ring, because the patentees, Campbell et al, claim that an even larger gap should exist between the outside diameter of the stiffening ring and the outside diameter of the subassembly.

U.S. Pat. No. 5,178,633-Peters dated Jan. 12, 1993 discloses another concept where a continuous metal band is heat shrinked onto the outside diameter of the subassembly. As disclosed by Dr. Joseph E. Shigley in his text, *Mechanical Engineering Design* 3rd ed., McGraw-Hill Book Co., New York, 1977, pp. 63–69, shrink fits cause significant radial and circumferential stresses in the inner member (orifice ring after shrink fit) and significant stresses can be induced in constrained bodies undergoing heating (orifice ring during shrink fit process). The disadvantage to this method of constraint is that it too requires that the orifice ring be thicker than it would if the constraint were to be applied without the press fit.

U.S. Pat. No. 4,863,460-Magladry dated Sep. 5, 1989 discloses a continuous metal stiffening ring covered by fabric, which can be electromagnetically deformed inwardly, clamping the suture ring to the subassembly. U.S. Pat. No. 4,743,253-Magladry dated May 10, 1988 is similar to the U.S. Pat. No. 4,863,460 disclosure, but utilizing a split ring. Both of these concepts present problems with manufacturing, particularly potential damage to the subassembly, acceptable stiffness characteristics, and biocompatibility.

In summary, there are several disadvantages to the current prior art design configurations of suture rings in heart valve prostheses. Some designs are inadequate because they require metal orifice rings instead of the preferred material, pyrolytic carbon. Other designs fail to maximize the internal diameter of the orifice ring, even while utilizing pyrolytic carbon. Further, some designs subject the pyrolytic carbon orifice rings to undesirable stresses and potential damage during manufacture.

SUMMARY OF THE INVENTION

A heart valve prosthesis is disclosed which has a compliant orifice ring, housing one or more leaflet(s). The outside diameter of the orifice ring has a channel shape. A fabric tube covers the channel portion of the outside diameter of the orifice ring. A single split metal stiffening ring covers the outside diameter of the fabric tube in the channel portion of the orifice ring. The stiffening ring has a clasp which locks upon engaging, making disassembly during implantation or service difficult. The shape of the clasp constrains the free ends of the stiffening ring so that it effectively has the same stiffness as a continuous ring. The outside diameter of the stiffening ring is contoured to increase its moment of inertia in bending, therefore, increasing its stiffness.

With the foregoing in mind, it is an object of the present invention to provide a heart valve prosthesis which is rotatable.

It is also an object of the present invention to provide a heart valve prosthesis with an orifice ring having a relatively large internal diameter.

Another object of the present invention is to provide a heart valve prosthesis that requires fewer, more easily manufactured components, with more rapid assembly than do prior art suture rings.

A further object of the present invention is to provide a heart valve prosthesis whereby the suture ring cannot be inadvertently separated from the subassembly during implantation.

Other objects and advantages of the present invention will become apparent from the following detailed description, taken with reference to the accompanying drawings.

BRIEF DESCRIPTION OF THE DRAWINGS

FIG. 1 is a cross-sectional view of the suture ring attached to the orifice ring;

FIG. 2 is a top perspective view of the stiffening ring in the locked position;

FIG. 3 is a top plan view of the locked stiffening ring of FIG. 1;

FIG. 4 is a bottom plan view of the locked stiffening ring of FIG. 1;

FIG. 5 is a fragmentary top view of the locked stiffening ring in detail greatly enlarged;

FIG. 6 is a fragmentary bottom view of the locked stiffening ring in detail greatly enlarged; and FIG. 7 is a cross-sectional view of an alternative suture ring attached to the orifice ring.

DESCRIPTION OF THE PREFERRED EMBODIMENTS

The following description is of the best mode presently contemplated for practicing the invention. This description is not to be taken in a limiting sense, but is made for the purpose of describing the general principles of the invention. The scope of the invention should be determined with reference to the claims. The preferred embodiment of the present invention will now be described with reference to the accompanying drawings. In the drawings, like numerals will be used to designate like parts throughout.

FIG. 1 depicts a cross-sectional view of the suture ring 10, attached to the orifice ring 11. The orifice ring 11 may house leaflets as disclosed in U.S. Pat. No. 4,950,287-Reif dated Nov. 12, 1991. The orifice ring has an outer circumferential surface 12 with a substantial annular groove 13. The orifice ring 11 has a first axial end 14 and a second axial end 15. Flanged surfaces 16 and 17 are formed at the intersection of the outer circumferential surface 12 and the annular groove 13.

The fabric tube 18 has an internal surface 19 and an external surface 20. The fabric tube 18 also has a first axial end 21 and a second axial end 22. The internal surface 19 of the fabric tube 18 directly contacts the flanged surfaces 16 and 17 and the annular groove 13 of the orifice ring 11.

The stiffening ring 23 has an internal circumferential surface 24, an external circumferential surface 25, a first axial end 26, and a second axial end 27. The radial thickness of the stiffening ring is greater at the first axial end 26 than it is at the second axial end 27. The fabric tube 18 is folded such that the external surface 20 of the fabric tube 18 directly contacts the external circumferential surface 25 of the stiffening ring 23.

The filler ring 28 is of basic annular configuration with internal circumferential surface 29, external circumferential surface 30, first axial end 31, and second axial end 32. The filler ring 28 is arranged so that the internal surface 29 thereof contacts the folded over internal surface 19 of the fabric tube 18. The first axial end 31, the second axial end 32, and the external surface 30 of the filler ring 28 all contact the external surface 20 of the fabric tube 18. Suture lines 33 and 34 fix the first axial end 21 and second axial end 22 of the fabric tube 18, such that the suture ring 10 remains intact.

Mode of Operation

FIG. 2 depicts a top perspective view of the stiffening ring 23. After machining, the outer circumferential surface 25 is put into compression by a method such as peening with glass beads. The stiffening ring is split by a method such as wire electrical discharge. This process causes the formation of a first radial end 35 and a second radial end 36. The radial ends 35 and 36 of the stiffening ring 23 are shown more clearly in the FIG. 3, a top plan view of the stiffening ring, and in FIG. 4, a bottom plan view of the stiffening ring.

The radial ends 35 and 36 of the stiffening ring 23 form serpentine shape such that a clasp mechanism is formed. This clasp mechanism is visualized more clearly in FIGS. 5 and 6, fragmentary top and bottom views of the stiffening ring, detail greatly enlarged, respectively. In this case, the two radial ends 35 and 36 of the stiffening ring 23 are right circular cylinders. The first radial end 35 articulates within the second radial end 36, forming a hinged joint type of constraint. This effectively makes the split ring as stiff as a continuous ring. The two radial ends 35 and 36 of the stiffening ring 23 can be dimensioned such that elastic deformation of the second radial end 36 occurs, causing the clasp mechanism to lock the first radial end 35 within the second radial end 36.

The radial thickness of the first axial end 26 of the stiffening ring 23 is greater than it is at the second axial end 27. This increases the moment of inertia in bending of the stiffening ring 23. Such a configuration having radial thickness of ring 23 greater at end 26 compared with radial thickness of end 27 consequently is more stiff than it would be if the entire stiffening ring 23 had the same radial thickness as the second axial end 27. Therefore, this increase in the moment of inertia in bending enables the use of a larger inside diameter of the orifice ring 11 (FIG. 1).

The present invention (FIG. 1) permits the use of an orifice ring 11 with a very thin radial thickness. This makes insertion of the leaflets safer and easier, since the orifice ring 11 is more compliant. It also increases the inside diameter of the orifice ring 11, which is highly desirable because of improved hemodynamics.

Assembly of the suture ring 10 (FIG. 1) is also facilitated by the use of a split stiffening ring 23. The subassembly (leaflets mounted in the orifice ring) is placed inside of the fabric tube 18. The stiffening ring 23 is unlocked by removing radial end 35 from radial end 36. The stiffening ring 23 is then passed around the external surface 20 of the fabric tube 18 containing the subassembly. The stiffening ring 23 is positioned within the annular groove 13 of the orifice ring 11 and the clasp mechanism is locked. The fabric tube 18 is then folded as depicted in FIG. 1, the filler ring 28 is inserted, and the fabric tube 18 is fixed with two suture lines 33 and 34.

Alternately, an annular shaped safety band 37 can be inserted around the outside diameter 25 of the stiffening ring 23 prior to final assembly as depicted in FIG. 7.

The assembled heart valve prosthesis is rotatable; it provides for an orifice ring 11 having a relatively large internal diameter. It requires fewer, more easily manufactured components, with more rapid assembly than do prior art suture rings. Also, the suture ring cannot be inadvertently separated from the subassembly during implantation.

In conclusion, the suture ring for heart valve prosthesis of the present invention includes a heart valve stiffening ring having a clasp engageable from unlocked position into locked position relative to annular members including a heart valve subassembly and fabric tube respectively cloth wrapped around the heart valve stiffening ring as represented in FIGS. 1 and 7 herewith. Alternatively, a safety band may be used or demonstrated in FIG. 7. The filler ring 28 is an outer annular ring of plastic or fabric material adapted to be fitted concentrically around the metal stiffening ring per se of FIG. 1. The filler ring 28 serves as a filler as a safety band collectively including the clasp of the stiffening ring and the tube of plastic or fabric material located with cloth around the metal heart valve locking ring per se of the configuration for a heart valve of FIGS. 1 and 7, for example a metal heart valve, respectively an aortic heart valve as disclosed by co-pending parent Design Patent Application Ser. No. 036,662-Reif filed Mar. 24, 1995, now U.S. Design Patent D-376,206-Reif dated Dec. 3, 1996, as well as Design Ser. No. 053,158-Reif filed Apr. 15, 1996. The heart valve locking configuration can be used with heart valves disclosed by U.S. Patent D-358,648-Reif dated May 23, 1995 as well as disclosures for a heart valve of Design Ser. No. 036,687-Reif filed Mar. 24, 1995, now U.S. Design Patent D-383,208-Reif dated Sep. 2, 1997, and a heart valve rotator disclosure of Design Ser. No. 036,665-Reif filed Mar. 24, 1995, now U.S. Patent Design Patent D-372,781-Reif dated Aug. 13, 1996.

The present invention is, of course, in no way restricted to the specific disclosure of the specification and drawings, but also encompasses any modifications within the scope of the appended claims.

What I claim is:

1. A suture ring for a heart valve prosthesis comprising:
    a heart valve split stiffening ring for a heart valve body, the ring having a locking clasp with first and second axial ends interchangeable complementary to each other from an unlocked position into an interlocked position of said split stiffening ring relative to a heart valve orifice ring juxtaposed therewith;
    a fabric tube located concentrically around the stiffening ring, the ring having at least two suture lines fixing the fabric tube in place therewith;
    a filler ring comprising an outer ring of fabric material positioned concentrically around the stiffening ring collectively surrounded by said fabric tube;
    said filler ring having at least one recess space therein axially open in only one direction;
    said fabric tube comprising cloth wrapped around the suture ring radially outwardly from the heart valve orifice ring;
    said heart valve orifice ring having an internal diameter relative to which a heart valve prosthesis is rotatable upon assembly therewith;
    said stiffening ring, filler ring, fabric tube, and at least two suture lines forming an assembly which cannot be inadvertently separated during implantation thereof.

2. A suture ring according to claim 1, wherein said clasp includes a fist axial end having a curved prong configuration that fits complementary to a second axial end having a socket configuration complementary to said prong configuration.

3. A suture ring according to claim 2, wherein said first and second axial ends of said clasp are right circular cylinders.

4. A suture ring according to claim 2, wherein said axial ends form a hinged joint type of constraint.

5. A suture ring according to claim 4, wherein the hinged joint type of constraint of the clasp effectively makes a split stiffening ring comparable to a continuous ring in stiffness.

6. A suture ring according to claim 2, wherein said first and second axial ends of the clasp have a complementary configuration such that elastic deformation of one axial end occurs causing said clasp to lock one radial end within the second axial end.

7. A suture ring according to claim 2, wherein a radial thickness of one axial end of the stiffening ring exceeds that of the second axial end, thereby increasing the moment of inertia in bending of the clasp and enabling the use of an enlarged inside diameter of said stiffening clasp relative to said heart valve orifice ring further providing for improved hemodynamics thereof.

8. A suture ring according to claim 1, in which said fabric tube is folded and includes a filler ring inserted therewith.

9. A suture ring according to claim 1, wherein said locking clasp with said first and second interlocked axial ends is positioned with an external annular groove of the heart valve orifice ring, said locking clasp being locked in place with said fabric tube being fixedly secured with said at least two suture lines.

10. A suture ring according to claim 1, further comprising a safety band formed collectively with said clasp and fabric tube around said heart valve stiffening ring.

* * * * *